United States Patent [19]

Rubin et al.

[11] 4,375,421

[45] Mar. 1, 1983

[54] VISCOUS COMPOSITIONS CONTAINING AMIDO BETAINES AND SALTS

[75] Inventors: Fred K. Rubin, Leonia; David Van Blarcom, West Milford, both of N.J.

[73] Assignee: Lever Brothers Company, New York, N.Y.

[21] Appl. No.: 312,439

[22] Filed: Oct. 19, 1981

[51] Int. Cl.$^3$ .................... C11D 1/90; C11D 1/94; C11D 3/04; C11D 17/08

[52] U.S. Cl. .................... 252/110; 252/89.1; 252/117; 252/133; 252/173; 252/174.14; 252/174.16; 252/174.19; 252/523; 252/526; 252/527; 252/541; 252/545; 252/546; 252/558; 252/DIG. 5; 252/DIG. 7; 252/DIG. 13; 252/DIG. 14; 252/DIG. 17; 424/70

[58] Field of Search .................... 252/89.1, 110, 117, 252/133, 153, 173, 174.14, 174.16, 174.19, 523, 526, 527, 541, 545, 546, 558, DIG. 5, DIG. 7, DIG. 13, DIG. 14, DIG. 17; 424/70

[56] References Cited

U.S. PATENT DOCUMENTS

| | | | |
|---|---|---|---|
| 3,328,307 | 6/1967 | Schmitz | 252/106 |
| 3,533,955 | 10/1970 | Pader | 252/153 |
| 3,554,916 | 1/1971 | Kerfoot | 252/545 |
| 3,594,323 | 7/1971 | Taylor | 252/545 |
| 3,876,563 | 4/1975 | Collins | 252/545 |
| 3,893,955 | 7/1975 | Hewitt | 252/551 |
| 3,980,769 | 9/1976 | Ghilardi et al. | 424/70 |
| 3,990,991 | 11/1976 | Gerstein | 252/542 |
| 4,003,857 | 1/1977 | Gorsich | 252/546 |
| 4,092,273 | 5/1978 | Inamorato | 252/548 |
| 4,107,067 | 8/1978 | Murphy et al. | 252/135 |
| 4,110,263 | 8/1978 | Lindemann | 252/545 |
| 4,122,043 | 10/1978 | Kersnar | 252/527 |
| 4,158,644 | 6/1979 | Hammerel | 252/547 |
| 4,181,634 | 1/1980 | Kennedy | 252/545 |
| 4,221,733 | 9/1980 | Melloh | 252/546 |
| 4,243,549 | 1/1981 | Messenger | 252/355 |

OTHER PUBLICATIONS

Lonza Product Information Bulletin, pp. 1–3, Lonzaine C (undated).
Product Information Bulletin from the Miranol Chemical Co., pp. 1–3, Mirataine CB (undated).
Product Bulletin from the Stepan Chemical Company, Amphosol CA (undated).

*Primary Examiner*—Dennis L. Albrecht
*Attorney, Agent, or Firm*—James J. Farrell

[57] ABSTRACT

Aqueous solutions containing alkylamido betaines and certain water-soluble inorganic or organic salts provide compositions of remarkably high viscosities. The inorganic salts suitable for this purpose are the sulfates of metals from Groups IA, IIA, IIB, and IIIA of the periodic table; sulfates of non-metallic ions; and alkali metal carbonates. Organic salts suitable in the present compositions include the citrates, tartrates, succinates, and carboxymethyloxysuccinates of metals from Groups IA, IIA, IIB and IIIA of the periodic table and the citrates, tartrates, succinates and carboxymethyloxysuccinates of ammonium ions. These salts have a synergistic viscosity-building effect on aqueous compositions containing alkylamido betaines in combination with micelle-forming anionic surfactants. Other salts increase the viscosity of aqueous solutions containing alkylamido betaines only in the presence of anionic surfactants. Suitable inorganic salts in this category include sulfates of metals from Group IB of the periodic table; alums; alkali metal sesquicarbonates; alkali metal tripolyphosphates and pyrophosphates; salts of halogen acids selected from the group consisting of potassium chloride and ammonium chloride; and alkali metal silicates. Suitable organic salts in this category include alkali metal salts of acetic acid and alkali metal salts of nitrilotriacetic acid.

84 Claims, No Drawings

VISCOUS COMPOSITIONS CONTAINING AMIDO BETAINES AND SALTS

BACKGROUND OF THE INVENTION

The present invention relates to viscous liquids, pastes, and gels useful in various cosmetic, toiletry, cleansing and other compositions. More specifically, the present invention relates to viscous liquids, pastes, and gel compositions containing as essential ingredients alkylamido betaines, certain salts, and water.

Many cosmetic, toiletry, and cleansing compositions contain amphoteric and zwitterionic surfactants. These surfactants may serve as detergents which either replace or are in addition to anionic detergents. Betaines constitute one of the more important classes of amphoteric and zwitterionic surfactants used in such compositions. Included in the class of betaine surfactants are alkylamido betaines, alkylamino betaines, and alkyl betaines.

These compounds have the following structures:

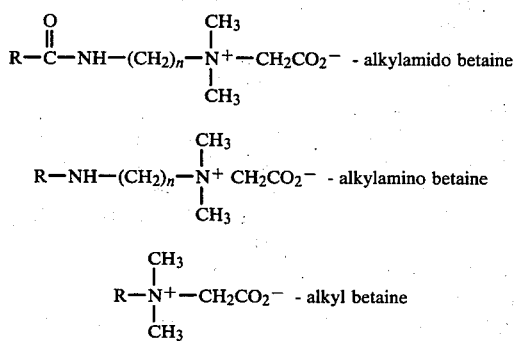

wherein R represents a fatty alkyl or alkenyl chain; n is an integer, usually 3.

For example, cocoamido betaine, cocoamino betaine and coco betaine are available from Lonza Incorporated, the Stepan Chemical Company, and the Miranol Chemical Co.

Sulfobetaines, wherein the carboxylate groups of the betaines described above are replaced by sulfonate groups, are also commercially available. For example, the structure of cocoamido sulfobetaine may be represented by the formula:

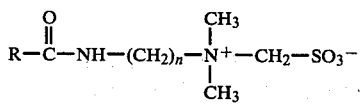

wherein R and n have the same meanings as above.

Betaines are useful in a variety of compositions as a result of numerous favorable properties. In particular, they are mild, high foaming, and biodegradable surfactants and wetting agents. In addition, they are compatible with high levels of detergency builders, electrolytes, alkalis and acids. This combination of properties makes betaines useful in a variety of cleansing and industrial compositions such as alkaline and acid cleaners, light and heavy duty cleaners, metal finishing compositions, electroplating compositions, etc. The use of betaines in heavy duty cleaners, for example, is described in U.S. Pat. No. 3,876,563.

Betaines also provide good conditioning to skin and hair. As a result, betaines are frequently used in shampoo, toiletry and cosmetic compositions. The use of betaines for these applications is described in U.S. Pat. Nos. 3,328,307, 3,980,769 and 4,110,263.

As a result of the compatibility of betaines with quaternary ammonium and other germicides, betaines are also used in disinfectant and sanitizing cleansers as well as in antibacterial scrubs. Textile finishing and dye compositions are also known to benefit from the beneficial wetting, conditioning and levelling action of betaines.

It is frequently desirable for a cleaning composition to contact dome-shaped or vertical surfaces for prolonged periods of time. Freely-flowing liquids are unsuitable for this purpose since they do not remain in contact with such surfaces long enough. In order to avoid this problem, thickeners are added to the cleansing composition in order to increase viscosity and to reduce the ability of the composition to flow. Some examples of cleansing compositions which are advantageously thickened for this reason are shampoos, dishwashing detergents, toilet bowl cleaners, wall cleaners, and the like.

In addition, viscous compositions such as gels are commercially advantageous. Many consumers prefer viscous liquids and gels to non-viscous liquids because of the impression of strength conveyed as well as other aesthetic qualities. Moreover, viscous liquids and gels can be dispensed by methods other than by simple pouring. For example, viscous liquids and gels can be dispensed from tubes by squeezing.

Traditionally, the viscosity of aqueous solutions has been increased by the addition of thickening agents such as proteins, pyrogenic silicas, polyoxyethylene polymers, and natural and synthetic cellulosic gums such as hydroxypropylcellulose, methylcellulose, carboxymethylcellulose and hydroxymethylcellulose. The use of such thickening agents is disadvantageous, however, in view of the high cost and difficulty in handling involved in the use of such agents. Moreover, if a clear viscous liquid, paste or gel is desired, the use of thickening usually adds to the opaqueness of the composition.

Viscous compositions which do not require traditional thickening agents are also known. An example of such a composition is described in Murphy et al, U.S. Pat. No. 4,107,067. These compositions are said to be especially well adapted for use as detergents which are directly applied to stains and soils on fabrics during pretreatment prior to aqueous laundering. The ingredients of the Murphy et al detergent include an electrolyte and a nonionic surfactant. The electrolyte may be an alkali metal halide, sulfate, carbonate, nitrate or phosphate. The nonionic surfactant is the condensation product of a polyalkylene oxide and an aliphatic or alkyl aromatic hydrophobic compound. According to Murphy et al, the addition of an appropriate amount of electrolyte converts concentrated aqueous liquid solutions of the nonionic surfactant to gelatinous liquids and flowable gels. Gelatinous liquids are defined in this patent as those having a Brookfield viscosity in the range of about 500 cps to 10,000 cps at 72° F. Flowble gels are defined as those which have Brookfield viscosities in the range of about 10,000 cps to 50,000 cps at 72° F.

Lonza Incorporated has disclosed another method for forming viscous compositions in the absence of traditional thickeners. A publication giving product information on Lonzaine C, which is a solution containing cocoamido betaine and NaCl, discloses that "Lonzaine C in combination with most anionic surfactants potentiates viscosity to permit formulations ranging from viscous liquids to ringing gels". The Lonza compositions are said to be useful in a variety of cosmetic, toiletry and detergent applications.

The Murphy et al patent and the Lonza publication are unusual in that they disclose viscous aqueous compositions in the absence of additional thickening agents. The Murphy et al patent, however, is restricted to viscous detergents containing polyalkylene oxide-type nonionic surfactants. The Lonza publication is restricted to viscous compositions which require anionic surfactants in addition to cocoamido betaine.

There is a need, therefore, for viscous compositions which contain amphoteric or zwitterionic surfactants and which require neither anionic detergents nor traditional thickening agents.

OBJECTS OF THE INVENTION

It is an object of the present invention to provide viscous compositions useful in cleansing, toiletry, cosmetic, and other applications.

It is a further object of the present invention to provide viscous liquid, paste and gel compositions in the absence of traditional thickening agents.

It is a further object of the present invention to provide a viscous liquid, paste, or gel containing an amphoteric surfactant.

It is a further object of the present invention to provide a viscous liquid, paste or gel wherein the presence of an anionic surfactant is optional.

SUMMARY OF THE INVENTION

These and other objects of the present invention as will be understood by the following description have been obtained by discovering that aqueous solutions containing alkylamido betaines and certain water-soluble inorganic or organic salts provide compositions of remarkably high viscosities. Accordingly, the present invention relates to a viscous liquid, paste or gel composition comprising:

(a) 5 to 25% by weight of one or more amido betaines represented by the formula:

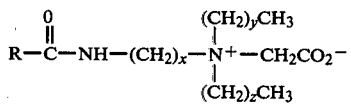

wherein:
(1) R is an alkyl or alkenyl chain containing 9 to 17 carbon atoms;
(2) x is an integer from 2 to 4;
(3) y is an integer from 0 to 3;
(4) z is an integer from 0 to 3;
(b) 5 to 40% by weight of one or more water-soluble inorganic or organic salts, the inorganic salt being selected from the group consisting of:
(1) sulfates of metal from groups Ia, IIa, IIb, and IIIa of the periodic table;
(2) sulfates of non-metallic ions;
(3) alkali metal carbonates.
the organic salt being incapable of forming micelles and being selected from the group consisting of the citrates, tartrates, succinates, and carboxymethyloxysuccinates of metals from Groups IA, IIA, IIB, and IIIA of the periodic table and the citrates, tartrates, succinates and carboxymethyloxysuccinates of ammonium ions.
(c) water to 100%;
the composition having a Brookfield viscosity of about 150 to about 1,500,000 cps at ambient temperatures.

It has also been found that a combination of the same salts listed above and micelle-forming anionic surfactants increase the viscosity of aqueous solutions containing alkylamido betaines synergistically. Therefore, in a second embodiment, the present invention relates to a viscous liquid, paste, or gel composition comprising:

(a) 5 to 25% by weight of one or more amido betaines represented by the formula:

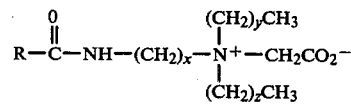

wherein:
(1) R is an alkyl or alkenyl chain containing 9 to 17 carbon atoms;
(2) x is an integer from 2 to 4;
(3) y is an integer from 0 to 3;
(4) z is an integer from 0 to 3;
(b) 2.5 to 40% by weight of one or more water-soluble inorganic or organic salts, the inorganic salt being selected from the group consisting of:
(1) sulfates of metal from Groups IA, IIA, IIB, and IIIA of the periodic table;
(2) sulfates of non-metallic ions;
(3) alkali metal carbonates.
the organic salt being incapable of forming micelles and being selected from the group consisting of the citrates, tartrates, succinates, and carboxymethyloxysuccinates of metals from Groups IA, IIA, IIB, and IIIA of the periodic table and the citrates, tartrates, succinates and carboxymethyloxysuccinates of ammonium ions.
(c) about 2.5 to 4.0% of a micelle-forming anionic surfactant; and
(d) water to make 100%;
the composition having a Brookfield viscosity of about 150 to about 1,500,000 cps at ambient temperatures.

Other salts increase the viscosity of aqueous solutions of alkylamido betaines only in the presence of anionic surfactants.

Accordingly, the present invention also relates to a viscous liquid, paste, or gel composition comprising:

(a) 5 to 25% by weight of one or more amido betaines represented by the formula:

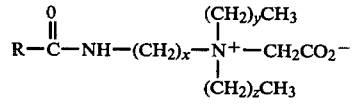

wherein:
(1) R is an alkyl or alkenyl chain containing 9 to 17 carbon atoms;
(2) x is an integer from 2 to 4;
(3) y is an integer from 0 to 3;
(4) z is an integer from 0 to 3;
(b) 0.25–4.0% by weight of one or more micelle-forming anionic surfactants.

(c) 5–40% by weight of one or more water-soluble inorganic or organic salt, the inorganic salt being selected from the group consisting of:
1. sulfates of metals from group IB of the periodic table;
2. alums;
3. alkali metal sesquicarbonates;
4. alkali metal tripolyphosphates and pyrophosphates;
5. salts of halogen acid selected from the group consisting of potassium chloride and ammonium chloride;
6. alkali metal silicates;

the organic salt being incapable of forming micelles and being selected from the group consisting of the alkali metal salts of acetic acid, and the alkali metal salts of nitrilotriacetic acid.

(d) water;

the composition having a Brookfield viscosity of 150 to 1,500,000 cps at ambient temperatures.

DETAILED DESCRIPTION OF THE INVENTION

The compositions of the present invention are viscous liquids, pastes, or gels. Viscous liquids are capable of flowing, although the flow is hindered. For the purposes of the present invention, the Brookfield viscosities of viscous liquids may be in the range of 150 to 10,000 cps, and preferably 500 to 7,500 cps at ambient temperatures.

Pastes and gels, on the other hand, are sufficiently viscous that they hardly flow at all unless pressure is applied. The pastes and gels of the present invention have Brookfield viscosities of about 10,000 to 1,500,000 cps, preferably about 100,000 to 1,000,000 and most preferably 200,000 to 700,000 at ambient temperatures.

The liquid, paste or gel may be clear or opaque. By clear is meant that the composition are transparent or translucent.

Many of the gels defined by the present claims are "ringing" gels. This means that they vibrate for short periods of time when they or their container is struck with sufficient force by an object.

The essential components of the broadest embodiment of the present invention are at least one alkylamido betaine, at least one salt as defined below, and water. The composition may also contain one or more optional components.

The concentration of the alkylamido betaines is 5 to 25% by weight and preferably 10 to 20% by weight. The concentration of the salt is 5 to 40% by weight and preferably 15 to 25% by weight. The remainder of the composition comprises water and any optional ingredients.

The concentration of the salt is selected at least in part on the basis of the viscosity desired. In order to form viscous liquids, the concentration of the salt is preferably about 10 to 19% by weight. When a thick paste or gel is desired, the concentration of the salt is preferably about 20 to 35% by weight.

The concentration of the betaine depends on the concentration and viscosity-building effectiveness of the salt and on the type of composition desired. Higher concentrations of betaine are used as lower amounts of salt or less effective salts are present and as higher viscosities are desired. In order to form a viscous liquid, the concentration of the betaine is usually less than about 15% by weight and generally between 10 and 15% by weight. If a thick paste or gel is desired, the concentration of the betaine is usually greater than about 15% and generally between 15 and 25% by weight.

The amido betaines useful in the present compositions may be represented by the following formula:

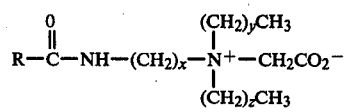

wherein:
R represents an alkyl or alkenyl chain containing 9 to 17 carbon atoms;
x is an integer from 2 to 4;
y is an integer from 0 to 3;
and z is an integer from 0 to 3.

The preferred value of x is 3. The preferred values for y and z are both 0. R preferably is a fatty group which contains 11 to 13 carbon atoms, most preferably in a straight chain. The preferable source of the R group is coconut oil. The preferred amido betaine may be represented by the following formula:

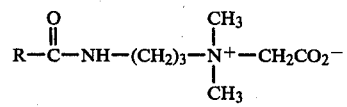

wherein R represents an alkyl or alkenyl chain containing 9 to 13 carbon atoms.

The alkylamido betaines useful in the present compositions are commercially available from Lonza Incorporated under the trademark Lonzaine C; from the Miranol Chemical Co. under the trademark Mirataine CB; and from the Stepan Chemical Co. under the trademark Amphosol CA. The alkylamido betaines are also relatively simple to prepare by well known techniques according to the following equations:

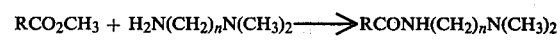

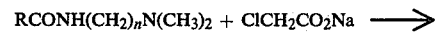

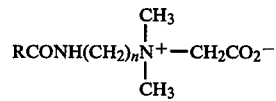

wherein R is a fatty alkyl group and n is 2 to 4.

The type of betaine suitable for use in the compositions of this invention is very specific. Most betaines are not thickened in the presence of salts. It has been discovered that aqueous solutions only of alkylamido betaines are thickened under these conditions. Examples of betaines which are not thickened by salts and which by themselves are, therefore, unsuitable for use in the present compositions include alkyl betaines, alkylamino betaines, alkyl sulfobetaines, alkylamino sulfobetaines, and alkylamido sulfobetaines.

The form in which the amido betaine exists in solution depends on the pH. Under acidic conditions, the carboxylate groups are protonated. Under basic conditions, the carboxylate groups are associated with whatever cations are available.

The salts of the present invention are water-soluble salts. By water-soluble is meant that the salt is soluble in water to at least the extent of the minimum concentrations recited in the present claims.

Surprisingly, not all salts are capable of increasing the viscosity of aqueous compositions containing the above-described amido betaines. The effect is very specific. Although a certain salt may increase viscosity, a closely related salt may not. No basis for predicting which salts will increase the viscosity of aqueous solutions of amido betaines is apparent.

Salts which increase the viscosity of aqueous solutions of alkylamido betaines include the soluble sulfates of metals from group IA, IIA, IIB and IIIA of the periodic table.

The preferred sulfates of metals from Group IA are sodium sulfate and potassium sulfate. The preferred sulfate of metals from Group IIA is magnesium sulfate. The preferred sulfate of metals from Group IIB is zinc sulfate. The preferred sulfate of metals from Group IIIA is aluminum sulfate. The most preferred sulfates of metals from Groups IA, IIA, IIB, and IIIA are sodium sulfate and magnesium sulfate.

The term "sulfate" in the present context includes ions related to sulfates such as bisulfate and thiosulfate. The preferred bisulfates and thiosulfates are sodium bisulfate and sodium thiosulfate.

The cation of the sulfate may also be non-metallic. Suitable examples of non-metallic cations include ammonium, sulfonium, and phosphonium.

The preferred non-metallic ion is ammonium ion. The term "ammonium" refers to $NH_4$ as well as to substituted ammonium. Thus, ammonium sulfates may be represented by the formula:

$$[R_a R_b R_c R_d N^+]_2 SO_4^=$$

In the formula, $R_a$, $R_b$, $R_c$ and $R_d$ may independently be H, $C_1$ to $C_4$ alkyl, or $C_2$ to $C_4$ hydroxyalkyl.

Suitable ammonium groups include $NH_4$; methylammonium, dimethylammonium, trimethylammonium and tetramethylammonium; ethylammonium, diethylammonium, triethylammonium and tetraethylammonium; and ethanolammonium, diethanolammonium, triethanolammonium and tetraethanolammonium. The preferred ammonium sulfates are those in which all of the R groups are hydrogen and those in which one or more of the R groups is 2-hydroxyethyl, the remaining R groups being H.

The salt useful in the present compositions may also be an alkali metal carbonate. Suitable alkali metal carbonates include potassium carbonate and sodium carbonate.

The salt of the present compositions may also be an organic salt. Organic salts refer to salts in which the anion contains one or more organic groups. The cation may be metallic or non-metallic. Suitable examples of organic salts containing metallic cations include the citrates, tartrates, succinates and carboxymethyloxysuccinates of metals from Groups IA, IIA, IIB, and IIIA.

The cation of the organic salt may also be non-metallic. Suitable examples of organic salts containing non-metallic cations include the ammonium citrates, tartrates, and succinates.

The term "ammonium" refers to $NH_4$ as well as to substituted ammonium. Thus, ammonium ions may be represented by the formula:

$$R_a R_b R_c R_d N^+$$

In the formula, $R_a$, $R_b$, $R_c$ and $R_d$ may independently be H, $C_1$ to $C_4$ alkyl, or $C_2$ to $C_4$ hydroxyalkyl.

Suitable ammonium groups include $NH_4$; methylammonium, dimethylammonium, trimethylammonium and tetramethylammonium; ethylammonium, diethylammonium, triethylammonium and tetraethylammonium; and ethanolammonium, diethanolammonium, triethanolammonium and tetraethanolammonium. The preferred ammonium ions are those in which all of the R groups are hydrogen and those in which one or more of the R groups is 2-hydroxyethyl, the remaining R groups being H.

Suitable organic salts include sodium citrate, sodium tartrate, sodium succinate, potassium citrate, potassium tartrate, potassium succinate, ammonium citrate, ammonium tartrate, ammonium succinate, ethanolammonium citrate, ethanolammonium tartrate, ethanolammonium succinate, diethanolammonium citrate, diethanolammonium tartrate, diethanolammonium succinate, triethanolammonium citrate, triethanolammonium tartrate and triethanolammonium succinate. A preferred organic salt is sodium citrate.

Particularly useful organic salts include the salts of carboxymethyloxysuccinic acid described in co-assigned U.S. Pat. No. 3,692,685, which is incorporated herein by reference. Typical of such materials are trisodium carboxymethyloxysuccinate, tripotassium carboxymethyloxysuccinate, trilithium carboxymethyloxysuccinate, triammonium carboxymethyloxysuccinate, the monoethanolamine salt of carboxymethyloxysuccinic acid, the diethanolamine salt of carboxymethyloxysuccinic acid, the triethanolamine salt of carboxymethyloxysuccinic acid, the tetramethylammonium salt of carboxymethyloxysuccinic acid, tri(ethylammonium) carboxymethyloxysuccinate, the monoisopropanolamine salt of carboxymethyloxysuccinic acid, the diisopropanolamine salt of carboxymethyloxysuccinic acid, monosodium dipotassium carboxymethyloxysuccinate, disodium monopotassium carboxymethyloxysuccinate, the morpholine salt of carboxymethyloxysuccinic acid, and the like.

The organic salts of the inventive compositions are incapable of forming micelles. Thus, anionic detergents such as alkyl sulfates, alkenyl sulfates, aralkyl sulfates, and alkaryl sulfonates, wherein the alkyl and alkenyl groups are derived from a fatty acid, and the corresponding ether sulfates are excluded from the list of salts recited in the claims directed to the broadest embodiment of this invention.

Although the presence of anionic surfactants is not necessary and in some cases not desirable in the compositions, it has unexpectedly been found that there is a synergistic effect when both an anionic surfactant and one or more of the inorganic or organic salts identified above are present together with an alkylamido betaine. That this is so can clearly be seen from Example 3. Compositions 3A, 3B, and 3C all contain 15% by weight of cocoamido betaine and water. In addition, Composition 3A contains 15% sodium sulfate and has a Brookfield viscosity of 175 cps at ambient temperatures. Composition 3B contains, in addition to the betaine and water, 2.4% alpha olefin sulfonate and has a Brookfield viscosity at ambient temperatures of 55 cps. Composition 3C contains, in addition to the betaine and water, 5% sodium sulfate and 2.4% alpha olefin sulfonate and has a Brookfield viscosity at ambient temperatures of 2600 cps. The viscosity of 3C, which contains both sodium sulfate and alpha olefin sulfonate, is clearly greater than what would be expected for combining compositions 3A and 3B, which separately contain sodium sulfate and alpha olefin sulfonate, respectively. It should be noted that composition 3C is unexpectedly viscous although it has one-third the amount of sodium sulfate as composition 3A. Therefore, one can obtain more highly viscous compositions at lower salt concentrations by adding a small amount of an anionic surfactant.

In view of this synergism, a second embodiment of the present invention is the formulation of the viscous liquid, paste, and gel compositions as described above, but additionally containing 0.25 to 4.0% by weight of micelle-forming anionic surfactants.

The salts which exhibit synergism in the presence of anionic surfactants in the present compositions are the same as those, given above, which unexpectedly thicken the compositions in the presence of alkyl and alkenylamido betaines in the absence of anionic surfactants.

The anionic surfactants which may optionally be added to the compositions and which, together with the salt, synergistically enhance the viscosity, may be any anionic surfactant capable of forming micelles in aqueous solutions. Preferred anionic detergents are those that are sulfonated and sulfated. The sodium, potassium, magnesium, calcium, ammonium, mono-, di- and triethanolamine salts of sulfated fatty alcohols, as well as these salts of sulfated aralkyl and sulfonated alkaryl compounds, all of which have fatty chains containing from 12 to 21 carbon atoms, are especially preferred. The sulfates described above may be the corresponding sulfate ethers wherein each molecule contains an average of from 1 to 12 and preferably 2 to 3 ethylene oxide units.

Suitable sulfated fatty alcohols include sodium lauryl sulfate, ammonium lauryl sulfate, sodium tallow alcohol sulfate and ammonium tallow alcohol sulfate.

Suitable sulfonated alkaryl compounds include sodium dodecylbenzene sulfonate, triethanolamine dodecylbenzene sulfonate and sodium laurylbenzene sulfonate.

Suitable ether sulfates include the sodium, potassium, magnesium, calcium, ammonium, mono-, di-, and triethanol amine salts of alcohol ethoxy sulfates. The alcohol in the ethoxy sulfates may be any fatty alcohol containing 10 to 18 carbon atoms, preferably 12 to 15 carbon atoms, and most preferably 12 carbon atoms. Preferred ether sulfates include sodium and ammonium lauryl ethoxy sulfate (2 moles E.O.), sodium and ammonium lauryl ethoxy sulfate (3 moles E.O.) and sodium and ammonium lauryl ethoxy sulfate (12 moles E.O.).

The anionic surfactants may be olefin sulfonates such as alpha olefin sulfonates. Suitable alpha olefin sulfonates include the sodium salt of alpha olefin sulfonate sold under the trademark Bioterge AS40 by the Stepan Co.; Surco AOS by Onyx-Millmaster Co.; AOS by Ethyl Corporation; or Sulframine by Witco Co. The structure of alpha olefin sulfonates may be represented by the formula R—CH=CH—SO$_3$Na wherein R is an alkyl or alkenyl group containing 10 to 14 carbon atoms.

Secondary alkane sulfonates containing 13 to 18 carbon atoms may also be used as the anionic surfactant. Suitable secondary alkane sulfonates include the sodium salt of secondary alkane sulfonate sold under the trademark Hostapur SAS-60 by American Hoechst Corporation.

Useful anionic surfactants also include the xylene/toluene sulfonates. Suitable examples include sodium xylene sulfonate, sodium toluene sulfonate, ammonium xylene sulfonate, ammonium toluene sulfonate, and mixtures of these sulfonates. These compounds are often present in detergent compositions as hydrotropes.

Salts of fatty acids, i.e., soaps, are also useful in the present compositions. Suitable soaps include sodium stearate, sodium tallowate, as well as the potassium, ammonium and mono-, di-, and triethanolamine salts of these acids. Mixtures of soaps are also useful.

Surfactants other than sulfates and sulfonates may be used. For example, the anionic surfactant may be of the phosphate mono- or diester type. These esters may be represented by the following formulas:

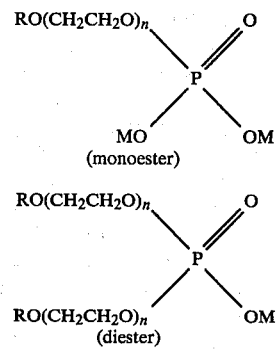

wherein:
R is a fatty chain containing 10 to 18 carbon atoms;
n is an integer from 0 to 5; and
M is any suitable cation such as alkali metal, ammonium and hydroxyalkyl ammonium.

Phosphate esters suitable in the present compositions include those sold under the trademark Gafac surfactants by the GAF Corporation.

The anionic surfactant may also be of the type wherein a fatty chain is attached to the anion of a carboxylic acid. Suitable anions of carboxylic acids include succinate, sulfosuccinate, and sarcosinate. Some typical surfactants of this type include sodium oleyl succinate, ammonium lauryl sulfosuccinate, and sodium N-lauryl sarcosinate.

When anionic surfactants are present in the compositions, less salt is used in order to achieve the same viscosity level. Thus, as little as 2.5% by weight of the salt may be used. In order to form a viscous liquid containing an anionic surfactant, the concentration of the salt is preferably about 5 to 9% by weight. In order to form a thick paste or gel, the concentration of the salt is preferably about 10 to 19% by weight.

The concentration of the amido betaine depends on the concentration and identity of the salt and on the viscosity desired. Higher concentrations of betaine are used as lower amounts of salt or less effective salts are present and as higher viscosities are desired. In order to form a viscous liquid, usually less than about 13% by weight of the amido betaine is present in the composition and generally between about 5 and 13%. When a thick paste or gel is desired, usually more than about 13% of the amido betaine is present and generally between about 13 and 20%.

A further embodiment of the present invention is based on the discovery that some salts thicken compositions containing amido betaines only in the presence of anionic surfactant. Thus, these compositions contain as essential components an amido betaine, a salt, an anionic surfactant, and water. This embodiment differs from that just described in that in the previous embodiment the anionic surfactant is optional while in the present embodiment the anionic surfactant is essential.

The amino betaine may be any of those described above as being useful in compositions of the present invention where anionic surfactants are absent or optional. The anionic surfactants may be any of those described above for use in compositions which optionally contain anionic surfactants.

Salts which require the presence of anionic surfactants to promote thickening of aqueous compositions containing amido betaines include soluble sulfates of metals from Group IB of the periodic table such as copper sulfate and silver sulfate; water-soluble alums such as potassium aluminum sulfate with the formula $KAl(SO_4)_2.12H_2O$; alkali metal sesquicarbonates such as sodium sesquicarbonate; complex phosphate salts such as sodium tripolyphosphate, tetrapotassium pyrophosphate, mixtures of tetrapotassium and tetrasodium pyrophosphate, especially those in the ratio of 8:1, the ammonium and hydroxyalkylammonium salts of these phosphates, and mixtures of these phosphate salts; certain salts of halogen acids selected from the group consisting of potassium chloride, and ammonium chloride; and alkali metal silicates such as sodium silicate. The ratio of silica to sodium oxide in the sodium silicate may be greater than one or less than one but is preferably greater than one. Some suitable sodium silicates include those with ratios of silica to sodium oxide of 2.4, 3.22, 2.0, and 2.88. These are available from the Philadelphia Quartz Corporation under the trade names sodium silicate RU, sodium silicate N, sodium silicate D, and sodium silicate K, respectively. The alkali metal silicate may also be potassium silicate. Some suitable potassium silicates include those with ratios of silica to potassium oxide of 2.50, 2.10, and 2.20. These are sold by the Philadelphia Quartz Corporation under the trade names Kasil 1, Kasil 6, and Kasil 88, respectively.

The salts which require the presence of anionic surfactants in the present compositions may also be organic salts. The organic salts in this class include the alkali metal salts of acetic acid, and of nitrilotriacetic acid.

The preferred alkali metal salts of acetic acid are sodium acetate and potassium acetate. The preferred alkali metal salts of nitrilotriacetic acid are sodium nitrilotriacetic acid and potassium nitrilotriacetic acid.

The concentration of the amido betaines in the compositions which require anionic surfactants is 5 to 25% by weight and preferably 10 to 20% by weight.

The concentration of the micelle-forming anionic surfactant is 0.25 to 4.0% and preferably 1 to 2.5%. The concentration of the salts is 5 to 40% by weight and preferably 15 to 25% by weight.

As with the compositions which do not contain anionic surfactants or which optionally contain anionic surfactants, the compositions which require the presence of an anionic surfactant may be in the form of a viscous liquid, paste, or gel. The viscosity may range from 150 to 1,500,000 cps at ambient temperatures. At the low end of the viscosity range are the viscous liquids. At the upper end are the pastes or gels.

The concentration of the salt depends on the type of composition desired. In order to form a viscous liquid, the concentration of the salt is preferably 10 to 19% by weight. If a paste or gel is desired, the concentration of the salts is preferably about 20 to 35% by weight.

The concentration of the betaine depends on the concentration and identity of the salt and on the type of composition desired. Higher concentrations of betaine are used as lower amounts of salt or less effective salts are present and as higher viscosities are desired. In order to form a viscous liquid, the concentration of the betaine is usually less than about 15% by weight and generally between about 10 and 15% by weight. If a paste or gel is desired, the concentration of the betaine is usually greater than about 15% and generally between about 15 and 25% by weight.

It has also been found that certain salts are unsuitable for use in the present compositions under any circumstances. These salts are incapable of sufficient viscosity enhancement even in the presence of an anionic surfactant. Examples of inorganic salts which do not promote thickening under any of the present conditions include sodium bicarbonate, potassium bicarbonate, alkali metal nitrates such as sodium nitrate, borates such as sodium tetraborate ($Na_2B_4O_7.10H_2O$) oxyhalides such as sodium chlorate, some salts of halogen acids such as sodium bromide, sodium chloride and potassium iodide, some salts of phosphoric acids such as orthophosphates and dibasic sodium phosphate ($Na_2HPO_4$) and salts of dichromic acid such as potassium dichromate. Examples of organic salts which do not promote thickening under any of the present conditions include sodium benzoate, disodium EDTA, sodium oxalate, and monopotassium phthalate.

The viscous liquids, pastes and gels of this invention are relatively simple and uncomplicated to prepare. The most convenient method is to first prepare a solution of the salt. Heating is applied if necessary to effect dissolution. The alkylamido betaine is then added to the salt solution with agitation. A viscous liquid, paste, or gel forms immediately.

Generally, considerable air becomes entrained in the composition. Upon standing, however, the composition de-aerates resulting in a clear, stable product.

If anionic surfactants or other optional ingredients are added to the composition, they may be added before or after the addition of the alkylamido betaine.

The above preparation is but one of many ways in which the present compositions may be prepared. Although the order of mixing described is especially convenient, the various ingredients can be added to the water in any order. Alternatively, the ingredients can be blended together and the mixtures added to water.

The compositions of the present invention are useful in a large variety of applications. These applications include any composition which is advantageously thickened and in which the amido betaines, the salts, and, optionally, the anionic surfactants described above are effective ingredients.

The cocoamido betaines are amphoteric surfactants. Some of the salts useful in the present compositions, such as phosphates and carbonates, are detergency builders. Thus, the presently described compositions consisting essentially of alkylamido betaines, salts, water, and, optionally, anionic surfactants, are useful in a variety of cleansers in the absence of other ingredients which affect the essential nature of the cleanser—i.e., the absence of other surfactants and builders.

Various types of cleansers are advantageously thickened. Viscous cleansers remain in contact longer with surfaces, especially vertical or dome-shaped surfaces.

Thus, the present compositions are advantageously used as hand dishwashing products and a variety of other specialty cleaners such as toilet bowl cleaners, wall cleaners, etc. Depending on the application, anionic surfactants may be added to the compositions.

The present compositions may also be advantageously used in a variety of cosmetic and toiletry products. The compositions are especially useful in shampoos.

In addition to being useful without further ingredients, the compositions of this invention are compatible with a large variety of optional materials. For example, the present compositions are stable in the presence of acids and bases, even when the pH is as low as 0.1 or lower and as high as 13 or higher. Other adjuvants such as abrasives, disinfectants, colorants, perfumes, suds boosters, emollients and the like can be added to enhance consumer appeal and effectiveness.

Having generally described the invention, a more complete understanding can be obtained by reference to certain specific examples which are provided herein for purposes of illustration only and are not intended to limit the invention unless otherwise specified.

EXAMPLES

EXAMPLES 1 AND 2

The following compositions represent gels prepared from cocoamido betaine and salts.

|  | % by weight | | |
|---|---|---|---|
|  | 1A | 1B | 1C |
| Cocoamido betaine | 15.0 | 15.0 | 15.0 |
| Sodium sulfate | 20.0 | — | — |
| Zinc sulfate | — | 35.0 | — |
| Sodium citrate, dihydrate | — | — | 30.0 |
| Water | 65.0 | 50.0 | 55.0 |
|  | 100.0 | 100.0 | 100.0 |
| Brookfield viscosity (cps) | 122,000 | 45,000 | 850,000 |
| pH (as is) | 5.32 | 3.87 | 7.06 |

|  | % by weight | |
|---|---|---|
|  | 2A | 2B |
| Cocoamido betaine | 15.0 | 15.0 |
| Potassium carbonate | 15.0 | — |
| Ammonium sulfate | — | 20.0 |
| Water | 70.0 | 65.0 |
|  | 100.0 | 100.0 |
| Brookfield viscosity (cps) | 2,250 | 5,000 |
| pH (as is) | 10.98 | 5.28 |

EXAMPLE 3

This example illustrates the role of an anionic surfactant (alpha olefin sulfonate) in the formation of gels. When sodium sulfate is added at low concentration to a solution of cocoamido betaine, very little thickening occurs (3A). Similarly, low concentrations of alpha olefin sulfonate plus cocoamido betaine produce solutions of low viscosity (3B). However, low salt concentrations plus low anionic concentrations in combination with cocoamido betaine synergistically form high viscosity solutions and gels (3C–3F).

|  | 3A | 3B | 3C | 3D | 3E | 3F |
|---|---|---|---|---|---|---|
| Cocoamido betaine | 15.0 | 15.0 | 15.0 | 15.0 | 15.0 | 15.0 |
| Sodium sulfate | 15.0 | — | 5.0 | 8.0 | 10.0 | — |
| Alpha olefin sulfonate | — | 2.4 | 2.4 | 2.4 | 2.4 | 12.4 |
| Water | 70.0 | 82.6 | 77.6 | 74.6 | 72.6 | 72.6 |
| Brookfield viscosity (cps) | 175 | 55 | 2,600 | 21,500 | 45,000 | 21,000 |

While this example cites alpha olefin sulfonate as the anionic, the invention is not limited to this type of anionic, but applies to other anionics as well.

EXAMPLE 4

This example illustrates a gel-form acidic toilet bowl cleaner. For cleaning vertical surfaces, particularly where prolonged contact with the cleaner is required, a viscous product which adheres rather than flows down the surface, is of great advantage. The following composition represents such a product:

|  | % by weight |
|---|---|
| Cocoamido betaine | 15.0 |
| Sodium bisulfate | 20.0 |
| Colorant | 0.0003 |
| Water to | 100.0 |
| Brookfield viscosity (cps) | 44,000 |
| pH (as is) | 0.13 |

EXAMPLE 5

The following composition is a viscous alkaline liquid which is well suited for the cleaning of soiled vertical surfaces such as walls, house sidings, etc. While intended for undiluted application, it may be applied in aqueous dilution to wash floors, and other hard surfaces.

|  | % by weight |
|---|---|
| Cocoamido betaine | 12.0 |
| Sodium citrate, dihydrate | 20.0 |
| Sodium silicate, 2.4 ratio | 5.0 |
| Colorant | 0.0003 |
| Perfume | 0.2 |
| Water to | 100.0 |
| Brookfield viscosity (cps) | 2000 |
| pH (as is) | 11.5 |

EXAMPLE 6

The present invention is particularly useful for the preparation of highly viscous liquid or gel hand dishwashing products. Such "concentrates" can be dispensed from squeeze tubes or plastic containers and present novel departures from the conventional hand dishwashing or light duty liquids. Viscous hand dishwashing products are advantageous for cleaning soiled pots and pans, because such products adhere to vertical pot and pan surfaces and promote soil removal by virtue of their prolonged and intimate contact with the soil. A viscous hand dishwashing product thus can be effectively used for pretreating heavily soiled kitchenware.

The examples shown below represent hand dishwashing gels (6-A, 6-B, 6-C) and a conventional commercial hand dishwashing liquid control (6-D). The performance of these compositions, in terms of sudsing characteristics, were compared and found to be equal or superior to the commercial control. Assessment of sudsing characteristics was conducted by means of the Plunger Foam Breakdown Test which measures the durability of generated foams upon multiple additions of a fatty soil. Details of the Plunger Foam Breakdown Tests are as follows:

(1) Identical solutions of the experimental and the control detergents are prepared using distilled water.

(2) Portions of these detergent solutions of known concentration are then equally diluted in graduated cylinders using a stock solution of water having a known hardness.

(3) The graduated cylinders are then immersed in a water bath heated to 116° F., and allowed to reach temperature equilibrium.

(4) The detergent solutions are then agitated by mechanically operated plungers at identical speeds for the same period of time. The resulting foam volumes formed in each cylinder are then recorded.

(5) Equal increments of test soil are then added to each of the cylinders and plunger agitation is resumed for a fixed period.

(6) At the end of the period of agitation, the new foam volumes are recorded and the procedure in Step #5 is repeated until the foam volumes in the test cylinders have been depleted.

Results are expressed as the total of the foam volumes recorded for each detergent after addition of soil, as well as the number of soil increments required to deplete their foam levels. High foam volumes and numbers of soil increments are indicative of the better performing products. The presence of a control product permits performance comparisons between experimental detergents and a commercial product. To obtain a complete sudsing profile of a particular detergent product, different concentrations of the detergent are tested in hard and soft water.

| Hand Dishwashing (light Duty) Preparations | | | | |
|---|---|---|---|---|
| | % by weight | | | |
| | 6-A | 6-B | 6-C | 6-D (Control) |
| Cocoamido betaine | 15.0 | 15.0 | 15.0 | — |
| Lauryl dimethyl amine oxide | — | 5.0 | 4.0 | — |
| Sodium lauryl sulfate | 10.0 | — | — | — |
| Sodium alcohol ethoxy sulfate | — | — | — | 18.0 |
| Ammonium alcohol ethoxy sulfate | — | 5.0 | 2.0 | — |
| Ammonium xylene sulfonate | — | — | — | 2.0 |
| Ammonium alkylbenzene sulfonate | — | — | — | 13.5 |
| Lauric/myristic diethanolamide | — | — | — | 5.0 |
| Sodium sulfate | 15.0 | — | 15.0 | — |
| Sodium citrate, dihydrate | — | 10.0 | — | — |
| Colorant | 0.0002 | 0.0002 | 0.0002 | 0.0002 |
| Perfume | 0.15 | 0.15 | 0.15 | 0.15 |
| Water to | 100.0 | 100.0 | 100.0 | 100.0 |
| Foam Volume[1] (Plunger Foam Breakdown Test) and Soil Additions[1] | | | | |
| (a) 0.05% detergent conc. 175 ppm water hardness, ml | 492.5 | 422.5 | 402.5 | 645.0 |
| No. of soil additions | 14.5 | 10.0 | 10.0 | 14.0 |
| (b) 0.15% detergent conc. 25 ppm water hardness ml | 2125.0 | 1310.0 | 1107.5 | 1107.5 |
| No. of soil additions | 32.0 | 19.5 | 18.5 | 20.0 |

[1]Mean value of duplicate determinations.

The above data show that the gel products with their 21–25% surfactant content perform well against a commercial control product having a considerably higher surfactant content, i.e., 36.5%. Although the gel compositions do not exceed the sudsing performance of the commercial control product at low detergent concentration (0.05%) and higher water hardness (175 ppm), two of the gel compositions (6A and 6-B) outperform the commercial product at high detergent concentration (0.15%) and low water hardness (25 ppm).

Composition 6-A is an opaque thick, smooth paste, Compositions 6-B and 6-C are clear gels; Control Composition 6-D is a mobile liquid. The gel-form composition disperse readily with some agitation at water temperatures customary for hand dishwashing.

EXAMPLE 7

A viscous clear detergent-sanitizer gel was prepared as follows:

| | % by weight |
|---|---|
| Cocoamido betaine | 15.0 |
| Tetradecylbenzyldimethylammonium chloride, dihydrate | 2.0 |
| Ethyl alcohol | 0.5 |
| Sodium citrate, dihydrate | 25.0 |
| Colorant | 0.0004 |
| Water to | 100.0 |
| Brookfield viscosity (cps) | 92,000 |
| pH (as is) | 7.28 |

The detergent sanitizer composition of Example 7 is well suited for bathroom cleaning, because its viscosity will allow it to adhere and stay in prolonged contact with tile walls, toilet bowl, bath tub, etc.

EXAMPLE 8

This composition represents a gel-form shampoo which may be packed in and dispensed from a tube.

| | % by weight |
|---|---|
| Cocoamido betaine | 15.0 |
| Alpha olefin sulfonate | 2.4 |
| Sodium citrate, dihydrate | 15.0 |
| Colorant | 0.0002 |
| Perfume | 0.18 |
| Water to | 100.0 |
| Brookfield viscosity (cps) | 140,000 |
| pH (as is) | 6.4 |

EXAMPLE 9

Hand cleaners in gel form can be packed in wide mouth cans or jars, hence are convenient to use. They are not as messy as powder hand cleaners and can be formulated to be nonirritating to the skin and easily rinsible in water. The following formula represents a hand cleaning gel:

| | % by weight |
|---|---|
| Cocoamido betaine | 13.6 |
| Alpha olefin sulfonate | 2.2 |
| Sodium citrate, dihydrate | 13.5 |
| Calcite powder | 10.0 |
| Colorant | 0.0003 |
| Perfume | 0.15 |
| Water to | 100.0 |
| Brookfield viscosity (cps) | 166,000 |
| pH (as is) | 8.6 |

EXAMPLE 10

The following examples further illustrate that small additions of different anionics to cocoamido betaine have no marked viscosity enhancing effect, but that such anionic additions in the presence of salts have a decided effect on viscosity even though the illustrated salts, at the levels used, do not contribute to increase viscosity without anionics. The combination of salts plus anionics behave synergistically, increasing composition viscosity considerably beyond the sum of the viscosities obtained by salt alone plus anionics alone.

EXAMPLE 10

| | % by weight | | | | |
|---|---|---|---|---|---|
| | 10A | 10B | 10C | 10D | 10E |
| Cocoamido betaine | 15.0 | 15.0 | 15.0 | 15.0 | 15.0 |
| Sodium sulfate | 0 | 15.0 | 15.0 | 15.0 | 15.0 |
| Hostapur SAS-60[1] | 2.0 | 2.0 | 1.0 | 0.5 | 0 |
| $H_2O$ | 83.0 | 68.0 | 69.0 | 69.5 | 70.0 |
| Brookfield viscosity (cps) | 30 | 1,060,000 | 27,000 | 500 | 50 |

[1]Secondary alkane sulfonate available from American Hoechst Corp.

| | % by weight | | | | |
|---|---|---|---|---|---|
| | 10F | 10G | 10H | 10I | 10J |
| Cocoamido betaine | 15.0 | 15.0 | 15.0 | 15.0 | 15.0 |
| Sodium sulfate | 0 | 15.0 | 15.0 | 15.0 | 15.0 |
| Magnesium alkylbenzene sulfonate | 3.0 | 2.0 | 1.0 | 0.5 | 0 |
| $H_2O$ | 82.0 | 68.0 | 69.0 | 89.5 | 70.0 |
| Brookfield viscosity (cps) | 105 | 288,000 | 128,000 | 600 | 50 |

| | % by weight | | | | |
|---|---|---|---|---|---|
| | 10K | 10L | 10M | 10N | 10O |
| Cocoamido betaine | 15.0 | 15.0 | 15.0 | 15.0 | 15.0 |
| Sodium sulfate | 0 | 15.0 | 15.0 | 15.0 | 15.0 |
| Gafac LO-529[1] | 3.0 | 2.0 | 1.0 | 0.5 | 0 |
| $H_2O$ | 82.0 | 68.0 | 69.0 | 69.5 | 70.0 |
| Brookfield viscosity (cps) | 35 | 13,000 | 1,500 | 250 | 50 |

[1]Complex phosphate esters of nonionic surfactants of the ethylene-oxide-adduct type available from G.A.F.

| | % by weight | | |
|---|---|---|---|
| | 10P | 10Q | 10R |
| Cocoamido betaine | 15.0 | 15.0 | 15.0 |
| Sodium sulfate | 0 | 15.0 | 15.0 |
| Sodium alkylbenzene sulfonate $C_{12}-C_{14}$ | 2.0 | 2.0 | 0 |
| $H_2O$ | 83.0 | 68.0 | 70.0 |
| Brookfield viscosity (cps) | 15 | 56,000 | 50 |

EXAMPLE 11

The following examples illustrate the procedure used in preparing typical cocoamido betaine/salt and cocoamido betaine/salt/anionic surfactant gels:

EXAMPLE 11A

| Component | % by Weight |
|---|---|
| $H_2O$ | 65.0 |
| Sodium sulfate | 20.0 |
| Cocoamido betaine | 15.0 |
| | 100.0 |

In Example 11A the sodium sulfate is added to the entire quantity of water required in the composition. The salt/water mixture is then stirred with a mechanical paddle mixer until the salts dissolve. (If necessary, the solution may be heated to facilitate the dissolving process.) Cocoamido betaine is then added to the stirred salt solution. A clear gel instantly forms having a viscosity of 122,000 cps. (Brookfield Viscometer)

EXAMPLE 11B

| Component | % by Weight |
|---|---|
| $H_2O$ | 67.6 |
| Potassium acetate | 15.0 |
| Cocoamido betaine | 15.0 |
| Alpha olefin sulfonate* | 2.4 |
| | 100.0 |

*Bioterge AS-40 (Stepan)

In Example 11B, as in Example 11A, the cocoamido betaine is added to a solution of potassium acetate and water with mechanical paddle stirring. The anionic surfactant (alpha olefin sulfonate) is then added to the other three components resulting in a viscous product having a viscosity of 3,100 cps.

EXAMPLE 11C

| Component | % by Weight |
|---|---|
| $H_2O$ | 65.0 |
| Sodium bisulfate | 20.0 |
| Cocoamido betaine | 15.0 |
| | 100.0 |

Example 11C is prepared exactly the same as Example 11A. The resulting product is a clear gel having a viscosity of 44,000 cps.

EXAMPLE 11D

| Component | % by Weight |
|---|---|
| $H_2O$ | 67.8 |
| Copper sulfate | 15.0 |
| Cocoamido betaine | 15.0 |
| SAS-60* | 2.2 |

*SAS-60 (secondary alkane sulfonate)

Example 11D is prepared exactly the same as Example 11B. The resulting product is a viscous gel.

EXAMPLE 11E

| Component | % by Weight |
|---|---|
| $H_2O$ | 60.0 |
| CMOS** | 25.0 |
| Cocoamido betaine | 15.0 |

| Component | % by Weight |
| --- | --- |
| | 100.0 |

**Sodium salt of carboxymethyloxysuccinate.

Example 11E is prepared exactly the same as Example 11A. The resulting clear gel has a viscosity of 560,000 cps.

Having now fully described the invention, it would be apparent to one of ordinary skill in the art that many changes and modifications can be made thereto without departing from the spirit or scope of the invention as set forth herein.

What is claimed is:

1. A viscous liquid, paste, or gel composition comprising:
   (a) 5 to 25% by weight of one or more amido betaines represented by the formula:

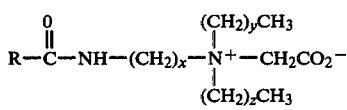

wherein:
   (1) R is an alkyl or alkenyl chain containing 9 to 17 carbon atoms;
   (2) x is an integer from 2 to 4;
   (3) y is an integer from 0 to 3;
   (4) z is an integer from 0 to 3;
   (b) 5 to 40% by weight of one or more water-soluble inorganic or organic salts, the inorganic salt being selected from the group consisting of:
   (1) sulfates of metal from groups Ia, IIa, IIb, and IIIa of the periodic table;
   (2) sulfates of non-metallic ions;
   (3) alkali metal carbonates.
   the organic salt being incapable of forming micelles and being selected from the group consisting of the citrates, tartrates, succinates, and carboxymethyloxysuccinates of metals from Groups IA, IIA, IIB, and IIIA of the periodic table and the citrates, tartrates, succinates and carboxymethyloxysuccinates of ammonium ions.
   (c) water to 100%;
   the composition having a Brookfield viscosity of about 150 to about 1,500,000 cps at ambient temperatures.

2. The composition of claim 1 wherein the gel is a ringing gel.

3. The composition of claim 1 wherein the concentration of the amido betaine is about 10–20% by weight.

4. The composition of claim 1, wherein the concentration of the salt is about 15–25% by weight.

5. The composition of claim 1 in the form of a viscous liquid having a Brookfield viscosity at ambient temperatures of 150 to 10,000 cps.

6. The composition of claim 1 in the form of a viscous liquid having a Brookfield viscosity at ambient temperatures of 500 and 7,500 cps.

7. The composition of claim 5 wherein the concentration of the salt is about 10 to 19% by weight.

8. The composition of claim 5 wherein the concentration of the amido betaine is about 10 to about 15% by weight.

9. The composition of claim 1 in the form of a paste or gel having a Brookfield viscosity at ambient temperatures of 10,000 to 1,500,000 cps.

10. The composition of claim 1 in the form of a paste or gel having a Brookfield viscosity at ambient temperatures of 100,000 to 1,000,000 cps.

11. The composition of claim 1 in the form of a paste or gel having a Brookfield viscosity at ambient temperatures of 200,000 to 700,000.

12. The composition of claim 9 wherein the concentration of the salt is about 20–35% by weight.

13. The composition of claim 9 wherein the concentration of the amido betaine is about 15% to about 25% by weight.

14. The composition of claim 1 wherein R in the formula for the amido betaine contains 11–13 carbon atoms.

15. The composition of claim 14 wherein R in the formula for the amido betaine is a fatty acid derived from coconut oil.

16. The composition of claim 1 wherein X in the formula for the amido betaine is 3.

17. The composition of claim 1 wherein both y and z in the formula for the amido betaine are 0.

18. The composition of claim 1 wherein the amido betaine is represented by the formula:

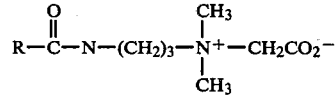

wherein R is a mixture of fatty acids from coconut oil.

19. The composition of claim 1 wherein the salt is selected from the group consisting of sodium sulfate, potassium sulfate, magnesium sulfate, ammonium sulfate, sodium bisulfate, sodium thiosulfate, zinc sulfate and aluminum sulfate.

20. The composition of claim 19 wherein the salt is selected from the group consisting of sodium sulfate, potassium sulfate, magnesium sulfate, and ammonium sulfate.

21. The composition of claim 1 wherein the salts are sulfates of non-metallic radicals represented by the formula:

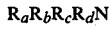

wherein each of $R_a$, $R_b$, $R_c$ and $R_d$ may be independently be H, $C_1$ to $C_4$ alkyl, or $C_2$ to $C_4$ hydroxyalkyl.

22. The composition of claim 21 wherein $R_a$, $R_b$, $R_c$ and $R_d$ all represent H.

23. The composition of claim 21 wherein at least one of $R_a$, $R_b$, $R_c$ and $R_d$ represents 2-hydroxyethyl and wherein any of $R_a$, $R_b$, $R_c$ and $R_d$ which does not represent 2-hydroxyethyl represents H.

24. The composition of claim 1 wherein the salt is an alkali metal carbonate selected from the group consisting of sodium carbonate and potassium carbonate.

25. The composition of claim 1 wherein the salt is an organic salt selected from the group consisting of the citrates, tartrates, succinates and carboxymethyloxysuccinates of alkali metals.

26. The composition of claim 25 wherein the alkali metal is sodium.

27. A viscous liquid, paste, or gel composition comprising:
   (a) 5 to 25% by weight of one or more amido betaines represented by the formula:

$$\underset{\underset{(CH_2)_zCH_3}{|}}{\overset{\overset{O}{\|}}{R-C}-NH-(CH_2)_x-\overset{\overset{(CH_2)_yCH_3}{|}}{N^+}-CH_2CO_2^-}$$

wherein:
(1) R is an alkyl or alkenyl chain containing 9 to 17 carbon atoms;
(2) x is an integer from 2 to 4;
(3) y is an integer from 0 to 3;
(4) z is an integer from 0 to 3:
(b) 2.5 to 40% by weight of one or more water-soluble inorganic or organic salts, the inorganic salt being selected from the group consisting of:
(1) sulfates of metal from Groups IA, IIA, IIB, and IIIA of the periodic table;
(2) sulfates of non-metallic ions;
(3) alkali metal carbonates.
the organic salt being incapable of forming micelles and being selected from the group consisting of the citrates, tartrates, succinates, and carboxymethyloxysuccinates of metals from Groups IA, IIA, IIB, and IIIA of the periodic table and the citrates, tartrates, succinates and carboxymethyloxysuccinates of ammonium ions.
(c) about 2.5 to 4.0% of a micelle-forming anionic surfactant; and
(d) water to 100%;
the composition having a Brookfield viscosity of about 150 to about 1,500,000 cps at ambient temperatures.

28. The composition of claim 27 in the form of a paste or gel having a Brookfield viscosity at ambient temperatures of 10,000 and 1,500,000 cps.

29. The composition of claim 27 in the form of a paste or gel having a Brookfield viscosity at ambient temperatures of 100,000 to 1,000,000 cps.

30. The composition of claim 27 in the form of a paste or gel having a Brookfield viscosity at ambient temperatures of 200,000 to 700,000.

31. The composition of claim 28 wherein the concentration of the salt is 10-19% by weight.

32. The composition of claim 28 wherein the concentration of amido betaine is about 13% to about 20% by weight.

33. The composition of claim 27 in the form of a viscous liquid having a Brookfield viscosity at ambient temperatures of 150 to 10,000 cps.

34. The composition of claim 27 in the form of a viscous liquid having a Brookfield viscosity at ambient temperatures of 500 to 7,500 cps.

35. The composition of claim 33 wherein the concentration of the salt is 5-9% by weight of the composition.

36. The composition of claim 33 wherein the concentration of amido betaine is about 5% to about 13% by weight of the composition.

37. The composition of claim 27 wherein R in the formula for the amido betaine contains 11-13 carbon atoms.

38. The composition of claim 37 wherein R in the formula for the amido betaine is a fatty acid derived from coconut oil.

39. The composition of claim 27 wherein X in the formula for the amido betaine is 3.

40. The composition of claim 27 wherein both y and z in the formula for the amido betaine are 0.

41. The composition of claim 27 wherein the amido betaine is represented by the formula:

$$\underset{\underset{CH_3}{|}}{\overset{\overset{O}{\|}}{R-C}-N-(CH_2)_3-\overset{\overset{CH_3}{|}}{N^+}-CH_2CO_2^-}$$

wherein R is a mixture of fatty acids from coconut oil.

42. The composition of claim 27 wherein the salt is selected from the group consisting of sodium sulfate, potassium sulfate, magnesium sulfate, ammonium sulfate, sodium bisulfate, sodium thiosulfate, zinc sulfate and aluminum sulfate.

43. The composition of claim 42 wherein the salt is selected from the group consisting of sodium sulfate, potassium sulfate, magnesium sulfate, and ammonium sulfate.

44. The composition of claim 27 wherein the salts are sulfates of non-metallic radicals represented by the formula:

$$R_aR_bR_cR_dN$$

wherein each of $R_a$, $R_b$, $R_c$ and $R_d$ may be independently be H, $C_1$ to $C_4$ alkyl, or $C_2$ to $C_4$ hydroxyalkyl.

45. The composition of claim 44 wherein $R_a$, $R_b$, $R_c$ and $R_d$ all represent H.

46. The composition of claim 44 wherein at least one of $R_a$, $R_b$, $R_c$ and $R_d$ represents 2-hydroxyethyl and wherein any of $R_a$, $R_b$, $R_c$ and $R_d$ which does not represent 2-hydroxyethyl represents H.

47. The composition of claim 27 wherein the salt is an alkali metal carbonate selected from the group consisting of sodium carbonate and potassium carbonate.

48. The composition of claim 27 wherein the salt is an alkali metal citrate selected from the group consisting of sodium citrate or potassium citrate.

49. The composition of claim 27 wherein the micelle-forming anionic surfactant contains a sulfate or sulfonate group.

50. The composition of claim 49 wherein the micelle-forming anionic surfactant is selected from the group consisting of sodium or magnesium lauryl sulfate, sodium or magnesium lauryl ethoxy sulfate, ammonium lauryl sulfate, ammonium lauryl ethoxy sulfate, sodium tallow alcohol sulfate, ammonium tallow alcohol sulfate, sodium tallow alcohol ethoxy sulfate and ammonium tallow alcohol ethoxy sulfate wherein each ethoxy sulfate contains 1 to 12 ethylene oxide units, sodium alpha olefin sulfonate containing 10 to 16 carbon atoms, sodium secondary alkane sulfonates containing 13 to 18 carbon atoms, sodium alkylbenzene sulfonate, ammonium alkylbenzene sulfonate and magnesium alkylbenzene sulfonate.

51. The composition of claim 50 wherein the micelle-forming surfactant is selected from the group consisting of sodium dodecylbenzene sulfonate, triethanolamine dodecylbenzene sulfonate, and sodium laurylbenzene sulfonate.

52. The composition of claim 27 wherein the micelle-forming anionic surfactant contains a phosphate group.

53. The composition of claim 52 wherein the surfactant is a mono- or diester represented by the formula:

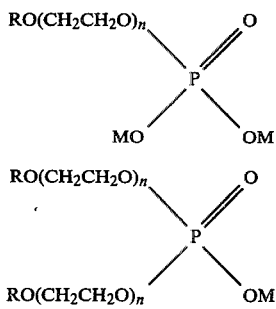

wherein R is a fatty chain containing 10 to 18 carbon atoms;
n is an integer from 0 to 5; and
M is any suitable cation.

54. The composition of claim 27 wherein the micelle-forming anionic surfactant is a soap.

55. A viscous, liquid, paste, or gel composition comprising:
(a) 5 to 25% by weight of one or more amido betaines represented by the formula:

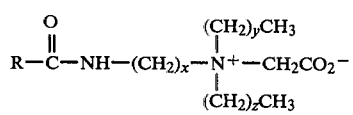

wherein:
(1) R is an alkyl or alkenyl chain containing 9 to 17 carbon atoms;
(2) x is an integer from 2 to 4;
(3) y is an integer from 0 to 3;
(4) z is an integer from 0 to 3;
(b) 0.25-4.0% by weight of one or more micelle-forming anionic surfactants.
(c) 5-40% by weight of one or more water-soluble inorganic or organic salt, the inorganic salt being selected from the group consisting of:
1. sulfates of metals from group IB of the periodic table;
2. alums;
3. alkali metal sesquicarbonates;
4. alkali metal tripolyphosphates and pyrophosphates;
5. salts of halogen acid selected from the group consisting of potassium chloride and ammonium chloride;
6. alkali metal silicates; the organic salt being incapable of forming micelles and being selected from the group consisting of the alkali metal salts of acetic acid, and the alkali metal salts of nitrilotriacetic acid.
(d) water;
the composition having a Brookfield viscosity of 150 to 1,500,000 cps at ambient temperatures.

56. The composition of claim 55, wherein the gel is a ringing gel.

57. The composition of claim 55, wherein the concentration of the salt is 15-25%.

58. The composition of claim 27, wherein the concentration of the amido betaine is 10-20% by weight.

59. The composition of claim 55 in the form of a paste or gel having a Brookfield viscosity at ambient temperatures of 10,000 to 1,500,000 cps.

60. The composition of claim 55 in the form of a paste or gel having a Brookfield viscosity at ambient temperatures of 100,000 to 1,000,000 cps.

61. The composition of claim 55 in the form of a paste or gel having a Brookfield viscosity at ambient temperatures of 200,000 to 700,000.

62. The composition of claim 59 wherein the concentration of the salt is about 20 to 35% by weight.

63. The composition of claim 60 wherein the concentration of the amido betaine is about 15% to about 25% by weight.

64. The composition of claim 55 in the form of a viscous liquid having a Brookfield viscosity at ambient temperatures of 150 to 10,000 cps.

65. The composition of claim 55 in the form of a viscous liquid having a Brookfield viscosity at ambient temperatures of 500 to 7,500 cps.

66. The composition of claim 64 wherein the concentration of the salt is 10-19% by weight.

67. The composition of claim 64 wherein the concentration of the amido betaine is about 10% to about 15% by weight.

68. The composition of claim 55 wherein R in the formula for the amido betaine contains 11-13 carbon atoms.

69. The composition of claim 68 wherein R in the formula for the amido betaine is a fatty acid derived from coconut oil.

70. The composition of claim 55 wherein x in the formula for the amido betaine is 3.

71. The composition of claim 55 wherein both y and z in the formula for the amido betaine are 0.

72. The composition of claim 55 wherein the amido betaine is represented by the formula:

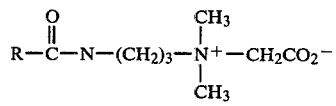

wherein R is a mixture of fatty acids from coconut oil.

73. The composition of claim 55 wherein the sulfates of metals from Group IB of the Periodic Table are selected from the group consisting of copper sulfate and silver sulfate.

74. The composition of claim 55 wherein the alum is potassium aluminum sulfate represented by the formula $KAl[SO_4]_2.12H_2O$.

75. The composition of claim 55 wherein the alkali metal sesquicarbonate is sodium sesquicarbonate.

76. The composition of claim 55 wherein the alkali metal tripolyphosphates and pyrophosphates are selected from the group consisting of sodium tripolyphosphate, tetrapotassium pyrophosphate and mixtures of tetrasodium pyrophosphate and tetrapotassium pyrophosphate.

77. The composition of claim 76 wherein the ratio of tetrapotassium pyrophosphate to tetrasodium pyrophosphate in the mixture of tetrapotassium pyrophosphate and tetrasodium pyrophosphate is 8:1.

78. The composition of claim 55 wherein the alkali metal silicates have a ratio of $SiO_2:Na_2O$ of greater than 1.

79. The composition of claim 55 wherein the salt of acetic acid is sodium acetate, potassium acetate, or trisodium nitrilotriacetate.

80. The composition of claim 55 wherein the micelle-forming anionic surfactant contains a sulfate or sulfonate group.

81. The composition of claim 80 wherein the micelle-forming anionic surfactant is selected from the group consisting of sodium lauryl sulfate, sodium lauryl ethoxy sulfate, ammonium lauryl sulfate, ammonium lauryl ethoxy sulfate, ammonium lauryl sulfate, ammonium lauryl ethoxy sulfate, sodium tallow alcohol sulfate, ammonium tallow alcohol sulfate, sodium tallow alcohol ethoxy sulfate, and ammonium tallow alcohol ethoxy sulfate wherein each ethoxy sulfate contains 1 to 12 ethylene oxide units, the sodium, ammonium and magnesium salts of alkylbenzene sulfonate, sodium alpha olefin sulfonate containing 10 to 16 carbon atoms and sodium secondary alkane sulfonate containing 13 to 18 carbon atoms.

82. The composition of claim 55 wherein the micelle-forming anionic surfactant contains a phosphate group.

83. The composition of claim 82 wherein the surfactant is a mono- or diester represented by the formula:

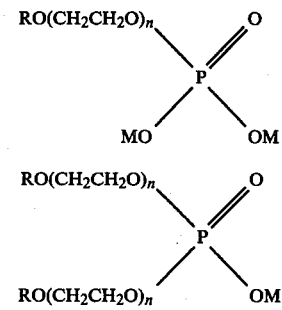

wherein R is a fatty chain containing 10 to 18 carbon atoms;

n is an integer from 0 to 5; and

M is any suitable cation.

84. The composition of claim 55 wherein the micelle-forming anionic surfactant is a soap.

* * * * *